(12) United States Patent
Newman et al.

(10) Patent No.: US 8,418,933 B2
(45) Date of Patent: Apr. 16, 2013

(54) BUBBLE PHASE AIR FRESHENER

(75) Inventors: Ron Newman, Murrieta, CA (US); Rachel Bukowski, Huntington Beach, CA (US)

(73) Assignee: Latitudes International, Rancho Dominguez, CA (US)

( * ) Notice: Subject to any disclaimer, the term of this patent is extended or adjusted under 35 U.S.C. 154(b) by 317 days.

(21) Appl. No.: 12/943,749

(22) Filed: Nov. 10, 2010

(65) Prior Publication Data

US 2012/0111968 A1   May 10, 2012

(51) Int. Cl.
*A61L 9/04* (2006.01)
*A61L 9/12* (2006.01)
*A61K 8/11* (2006.01)
*A61K 8/03* (2006.01)
*A61Q 13/00* (2006.01)
*C11D 3/50* (2006.01)

(52) U.S. Cl.
USPC .................. 239/44; 239/34; 512/1; 512/4

(58) Field of Classification Search ................ 239/6, 34, 239/35, 44, 60, 71, 302; 501/1, 4
See application file for complete search history.

(56) References Cited

U.S. PATENT DOCUMENTS

| | | | |
|---|---|---|---|
| 3,387,396 A | 6/1968 | Smith | |
| 4,961,493 A | 10/1990 | Kaihatsu | |
| 5,120,585 A | 6/1992 | Sutter et al. | |
| 5,140,450 A | 8/1992 | Nikaido | |
| 5,497,942 A | 3/1996 | Zingle et al. | |
| 6,604,835 B2 | 8/2003 | Zale | |
| 2004/0262418 A1 | 12/2004 | Smith et al. | |
| 2005/0175847 A1 | 8/2005 | Luten, III | |
| 2006/0131443 A1* | 6/2006 | Martinez et al. | 239/145 |
| 2009/0101729 A1* | 4/2009 | Newman | 239/44 |

* cited by examiner

*Primary Examiner* — Darren W Gorman
(74) *Attorney, Agent, or Firm* — Fulwider Patton LLP

(57) ABSTRACT

A fragrance bearing liquid, visible in a transparent container, supporting a floating colorized liquid bubble that is maintained in a substantially centered position. A wicking system transfers the fragranced liquid to the atmosphere.

20 Claims, 1 Drawing Sheet

BUBBLE PHASE AIR FRESHENER

This invention generally relates to fragrance delivery systems and more particularly, to a delivery system that achieves a particular visual effect. The system provides for a liquid bubble of contrasting color that appears suspended in and that remains substantially centered within a volume of fragrance bearing liquid.

BACKGROUND

A variety of fragrance delivery systems are known including liquid systems wherein the fragrance bearing liquid is simply exposed to or wicked into the atmosphere. In order to provide for an aesthetically pleasing appearance, the container of the fragrance bearing liquid may be relied upon for example by having a novel shape or a decoration thereon. Alternatively, the appearance of the actual fragrance-bearing liquid or liquids may be relied upon for aesthetic effect with the use of a transparent container. The liquid may be colorized or a plurality of immiscible liquids may be used whereby their contrasting colors provide a desired visual effect.

Liquid systems are known in which immiscible liquids are combined in order to provide either a layered or otherwise segregated appearance. Immiscible liquids of similar density will cause one or more of the liquids to form a bubble wherein such bubble will be suspended in the other non-bubble forming liquid. A challenge arises in providing an aesthetically pleasing display in which the bubbles tend not to migrate toward and become adhered to the inside surface of the container. Completely static systems cannot rely on an agitation of the liquids, for example by heating and cooling, in order to move suspended bubbles through the suspending liquid and thereby break any adhesions with the container surface. A static delivery system is needed which serves to control the relative positions of immiscible liquids having similar densities, and more particularly, to control their relative positions vis-a-vis the container's walls. Additionally, it is most desirable to provide a colorized bubble that appears to be suspended in a substantially clear liquid and that tends to maintain a relatively centered position within a containment vessel.

SUMMARY OF THE INVENTION

The present invention provides a fragrance delivery system wherein at least two immiscible liquids are visible and displayed in a transparent container. Two liquids are selected to have, or modified to have, similar densities so as not to be prone to forming layers. As a result, one of the liquids will appear as one or more bubbles that are suspended in the other liquid. In a preferred embodiment, the bubble forming liquid is colorized while the surrounding liquid is substantially colorless. Alternatively, the surrounding liquid may be colorized but sufficiently transparent so as to allow a more darkly colored or contrasting bubble to be seen. The invention provides for substantially reduced attraction between the container and the colored bubble forming phase such that a single liquid bubble is able to form and not break up and adhere to the side walls of the container. Ideally, this results in the bubble forming liquid remaining spaced apart from the walls of the container. The suspending liquid may be relied upon to support a fragrance, the release of which may be expedited by the use of a wicking system.

Optionally, the system may include a third mutually immiscible liquid. The bubble forming liquid and the liquid in which the bubble forming liquid is suspended are selected or modified such that the density of the bubble forming liquid is slightly less than the surrounding liquid to cause the bubble to float to the top of the surrounding liquid but not to form a separate layer. The third liquid is selected to have a substantially lower density so as to form a layer above the other two liquids. By selecting the layered liquids to be clear or of the same hue, the contrasting bubble will appear to be suspended in a more vertically centered position relative to the volume of liquid within the container while remaining spaced apart or at least curved away from the walls of the container with no more than a single point touching the wall of the container. One or both of the layer forming liquids may be relied upon to support a fragrance, the release of which may be expedited by the use of a wicking system.

An appropriate wicking material has a capillary or porous structure that avails a wicking path from below the surface of the liquids to above the surface of the liquids where evaporation can take place. Rattan core, sometimes referred to as reed is an example of a suitable wicking material.

The bubble forming liquid of the present invention is preferably aqueous while the container, or at least its inner surface, is rendered hydrophobic. This may be achieved by coating the surface with a silane compound, such as fluoro alkyl silane. Such surface treatment has been found to substantially prevent the suspended aqueous bubble from drifting into contact with or breaking up and drifting to the container walls and clinging to the container walls. The aqueous liquid is preferably colorized using food or cosmetic dyes, although color transfer from the bubble phase to the external phase can be problematic. While inorganic metal salts can provide for dramatic coloration, they have been found to clog wicking paths. If metal salts are used, EDTA, gluconic acid salts, and other hydrophilic chelating agents may be relied upon for stability to prevent or minimize the transfer of color to the surrounding liquid and for preventing competition for the metal by the fragrance components.

The liquid relied upon to suspend the aqueous bubble preferably includes a non-polar solvent, such as decamethylcyclopentasiloxane or various hydrocarbons, to minimize color transfer from the bubble. If a third, mutually immiscible liquid is to be used as a capping layer, an aryl alcohol is preferred as it has the poorest evaporation characteristics. The use of a third smaller top layer can provide a number of benefits. The liquid/liquid interface of the second and third phases can facilitate the coalescence of smaller bubble phase droplets for the formation of one large bubble. Additionally, such top layer could help modify the evaporation of the main (second) phase such that the bubble doesn't sink too quickly when evaporation begins as it is desirable to keep the bubble off the bottom of the container for as long as possible. If the main phase is somewhat volatile, then the top (third) phase would be formulated to act as a "capping layer", and then an aryl alcohol would be preferred. However, it has been discovered that a less volatile main phase yields superior evaporation characteristics as the specific gravity remains slightly greater than the bubble phase during evaporation, an aryl glycol ether is preferred to achieve such effect. Adjustment of the specific gravity of one or more of the liquids may be necessary in order to achieve the desired orientations. This is achieved by for example adding selectively miscible liquids, salts or other materials to one or more of the liquids. Additionally, materials may be added to all or to selected liquids for the purpose of pH adjustment, stabilization, metal ion sequestration, promotion of liquid separation, inhibition of microbial growth, prevention of oxidation, and for imparting or changing the color of one or more liquids including dyes and UV absorbers, etc.

A fragrance is added to one or both of the non-aqueous liquids. Generally defined, the fragrance comprises a substance or complex mixture of aroma chemicals, natural essential oils and other functional products, the sole purpose of which is to impart an odor or scent, or to counteract a malodor. The fragrance is preferably colorless, resistant to metal ion interactions and preferably has low water solubility. A simple construction fragrance with limited single note aroma chemicals is desirable as this results in enhanced wicking characteristics.

As such, the system of the present invention serves to continuously deliver a fragrance to the air while providing an aesthetically appealing visual effect in the form of a colorized bubble that appears to float and remain more or less centered in a volume of liquid. Horizontal centering can be enhanced if the bubble is sufficiently large compared to the horizontal dimensions of the glass container; or if reed wicks are inserted since the bubble will tend to "hug" the reed wicks. Vertical positioning is affected by temperature to the extent that the specific gravities of the various materials vary as a function of temperature. The specific gravities of the respective materials are therefore preferably adjusted such that a centered position in the vertical plane is achieved in a target temperature range of 70-75 F.

These and other advantages of the present invention will become apparent from the following detailed description of preferred embodiments which, taken in conjunction with the drawing, illustrate by way of example the principles of the invention.

DETAILED DESCRIPTION OF THE PREFERRED EMBODIMENTS

A preferred embodiment of the fragrance delivery system of the present invention is prepared as follows. The container in which the fragrance bearing liquids and the bubble forming liquid is to be contained is subjected to a surface treatment that renders at least its inside surface hydrophobic. This can for example be achieved with the use of a two component fluoroalkysilane system that is commercially available as SIVO®Clear from Evonik Degussa Corporation when applied in accordance with the manufacturer's instructions. The glass surface of the container is first cleaned to remove dust, grease, and other possible contaminants after which it is activated by treatment with a $Ce_2O_3$ slurry. The two components, SIVO®Clear K1 and SIVO®Clear K2 are mixed 1:1 by volume, applied to the surface and then allowed to dry for 20-30 hours.

The bubble-forming aqueous phase is prepared separately by combining deionized water, an organometallic colorant and a microbial inhibitor. Alternatively, a chelated-metallic water-soluble colorant may be relied upon in combination with a stabilizing system that provides for a pH of about 7 and metal-ion sequestration. The bubble-forming phase can be expected to achieve a specific gravity in the range of 1-1.05@20 C/20 C.

The principal non-aqueous phase is prepared separately by selecting a non-polar solvent such as for example decamethylcyclopentasiloxane, introducing thereinto a fragrance, oil-soluble UV absorbers and antioxidants, specific gravity adjusting components and coalescing aids. Specific gravity adjusting components preferably comprise alkyl and glycol ethers and derivatives thereof in a quantity sufficient to achieve the desired vertical position and bubble shape of the bubble phase. Coalescing aids may include isodecyl benzoate, 2,2,4-trimethyl-1,3-pentanediol monoisobutyrate, and methyl phenyl silicone fluids. The specific gravity of the principal non-aqueous phase is preferably adjusted in the range of 1-1.05@20 C/20 C.

If a third phase, i.e. a minor non-aqueous phase is to be relied upon to achieve the desired visual effect, a mutually immiscible substance such as phenoxy ethanol is combined with a specific gravity adjusting component such as dipropylene glycol dimethyl ether to achieve a specific gravity of about 0.95-1@20 C/20 C.

The phases are independently added to the coated container and thoroughly mixed. Depending on the fragrance and specific formulation, the system may take 12-24 hours to separate into distinct phases. Another 24 hours may be required to achieve total clarity of the non-aqueous layer. The container is sealed for storage and distribution. Prior to use, the container is opened and a wick or plurality of wicks is inserted into the liquid to draw out the fragrance.

Figure 1:
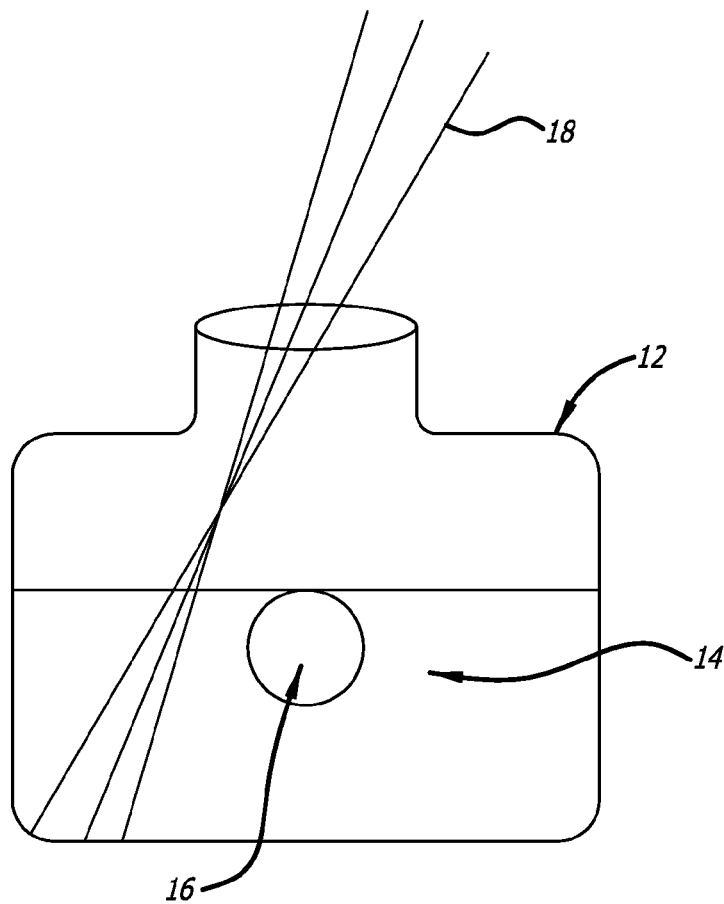
FIG. 1 is a representation of a preferred embodiment of the invention.

FIG. 1 is an illustration of a preferred embodiment of the fragrance delivery system of the present invention. A transparent container 12 contains a volume of a principal non-aqueous phase liquid 14 as well as a volume of colorized bubble-forming aqueous phase 16. The specific gravity of one or both of the phases is adjusted so that the bubble remains suspended within the principal phase while the treated container serves to maintain the bubble phase spaced apart from the walls of the container. A plurality of rattan sticks 18 are inserted into the liquid to draw out the fragrance containing principal phase.

Figure 2:
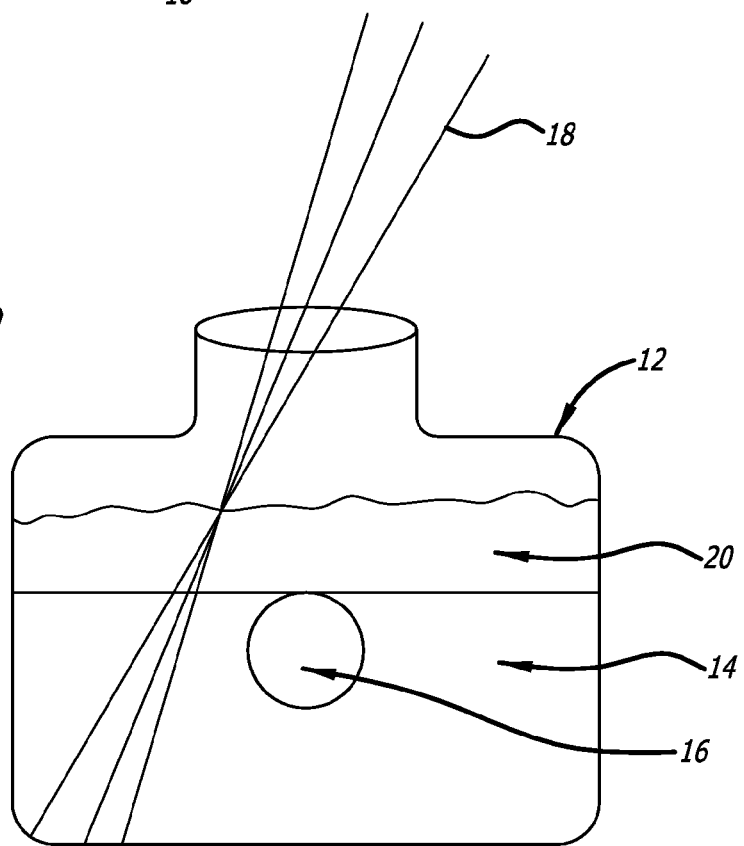
FIG. 2 is a representation of a preferred alternative embodiment of the invention.

FIG. 2 is an illustration of an alternative embodiment three phase fragrance delivery system in accordance with the present invention. A transparent container 12 contains a volume of a principal non-aqueous phase liquid 14 as well as a volume of colorized bubble-forming aqueous phase 16. The specific gravity of one or both of the phases is adjusted so that the bubble remains suspended within the principal phase while the treated container serves to maintain the bubble phase spaced apart from the walls of the container. A volume of minor non-aqueous liquid forms a topping layer 20 to maintain the bubble phase substantially centered within volume of clear phases. A plurality of rattan sticks 18 are inserted into the container to draw out the fragrance containing principal phase.

EXAMPLE

BOTTLE: A clear "rectangular" bottle is provided having an alkyl fluoro silane derived hydrophobic coating on its inner wall. The bottle is sealable with a rubber stopper.

FRAGRANCE: A simple Construction Phase-Transfer Screened "Marine" fragrance is provided.

BUBBLE PHASE SYNTHESIS: 0.5661 grams Copper Gluconate is added to 44.2 grams of Deionized Water. (Pale blue solution).

FORMULATION:

|  | Weight (grams) |
| --- | --- |
| Main Phase. | |
| Fragrance | 5 |
| 2-Phenoxy Ethanol | 11.2 |
| Diethylene Glycol Dimethyl Ether | 5 |
| Dipropylene Glycol n-Propyl Ether | 6.5 |
| Top Phase. | |
| Decamethylcyclopentasiloxane. | 11 |
| Bubble Phase. | |
| Copper Gluconate Solution | 13 |

The ingredients of main phase are mixed together until clear and introduced into the bottle. The top phase is then introduced into the bottle. Finally, the bubble phase is introduced into the bottle. The bottle is sealed and shaken vigorously. In approximately 16 hours the final product form will develop.

While particular forms of the invention have been described and illustrated, it will also be apparent to those skilled in the art that various modifications can be made without departing from the spirit and scope of the invention. As an example, additionally or alternatively, other classes of materials may be used that are mutually immiscible. Other treatments may be relied upon to render the container's surface hydrophobic. Alternative coloring systems may also be relied upon to provide contrasting coloration. Accordingly, it is not intended that the invention be limited except by the appended claims.

What is claimed is:

1. A fragrance delivery system, comprising:
   a container having a hydrophobic inner surface;
   an aqueous first liquid disposed in said container; and
   a second liquid, immiscible with said first liquid, disposed in said container, wherein said first and second liquids have substantially similar densities.

2. The fragrance delivery system of claim 1, wherein said second liquid supports a fragrance.

3. The fragrance delivery system of claim 1, further comprising a wicking system extending into said second liquid.

4. The fragrance delivery system of claim 1, wherein said second liquid comprises a non-polar solvent.

5. The fragrance delivery system of claim 4, wherein said non-polar solvent comprises a siloxane.

6. The fragrance delivery system of claim 1, wherein said first liquid is colorized.

7. The fragrance delivery system of claim 6, wherein said colorization is achieved with lipophobic organometallic colorants.

8. The fragrance delivery system of claim 1, wherein said inner surface of said container is coated with a silane.

9. The fragrance delivery system of claim 8 wherein said silane comprises fluoro alkyl silane.

10. The fragrance delivery system of claim 1, further comprising a third liquid, such third liquid being mutually immiscible with said first and second liquid and having a density less than said first and second liquids.

11. The fragrance delivery system of claim 10, wherein said third liquid comprises polyoxyethylene alkyl aryl ether.

12. The fragrance delivery system of claim 10, wherein said third liquid comprises. phenoxy ethanol.

13. A fragrance delivery system, comprising a colorized liquid bubble suspended in a clear fragrance bearing liquid, wherein said liquids are contained in a container which serves to maintain said bubble in a substantially centered position therein.

14. The fragrance delivery system of claim 13, wherein said liquid bubble is immiscible with said fragrance bearing liquid.

15. The fragrance delivery system of claim 13, wherein said liquid bubble is aqueous.

16. The fragrance delivery system of claim 15, wherein said container has an interior surface that is hydrophobic.

17. The fragrance delivery system of claim 16, wherein said interior surface of said container is coated with a silane.

18. The fragrance delivery system of claim 13, wherein said liquid bubble and said fragrance bearing liquid have substantially similar specific gravities.

19. The fragrance delivery system of claim 13, comprising a third liquid that forms a layer above said fragrance bearing liquid.

20. The fragrance delivery system of claim 13, wherein said liquid bubble includes lipophobic organometallic colorants.

* * * * *